United States Patent
Vijayagopal et al.

(10) Patent No.: US 9,421,385 B2
(45) Date of Patent: Aug. 23, 2016

(54) THERAPY DELIVERY ARCHITECTURE FOR IMPLANTABLE MEDICAL DEVICE

(71) Applicant: Cardiac Pacemakers, Inc., St. Paul, MN (US)

(72) Inventors: Ramprasad Vijayagopal, Shoreview, MN (US); Nicholas J. Stessman, Minneapolis, MN (US); William J. Linder, Golden Valley, MN (US); Ron A. Balczewski, Bloomington, MN (US); Keith R. Maile, New Brighton, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 32 days.

(21) Appl. No.: 13/945,109

(22) Filed: Jul. 18, 2013

(65) Prior Publication Data
US 2014/0052207 A1   Feb. 20, 2014

Related U.S. Application Data

(60) Provisional application No. 61/683,806, filed on Aug. 16, 2012.

(51) Int. Cl.
*A61N 1/372* (2006.01)
*A61N 1/36* (2006.01)
(Continued)

(52) U.S. Cl.
CPC ........... *A61N 1/372* (2013.01); *A61N 1/36125* (2013.01); *A61N 1/36185* (2013.01); *A61N 1/378* (2013.01)

(58) Field of Classification Search
CPC ........ A61N 1/05; A61N 1/0551; A61N 1/08; A61N 1/36; A61N 1/3605; A61N 1/362; A61N 1/378
USPC .................................. 607/9, 60, 66, 70, 116
See application file for complete search history.

(56) References Cited

U.S. PATENT DOCUMENTS

| 4,033,332 A | * | 7/1977 | Hardway et al. | 600/535 |
| 4,200,104 A | * | 4/1980 | Harris | 606/35 |

(Continued)

FOREIGN PATENT DOCUMENTS

| CN | 104582790 A | 4/2015 |
| WO | WO-2006107848 A2 | 10/2006 |
| WO | WO-2014028162 A1 | 2/2014 |

OTHER PUBLICATIONS

"International Application Serial No. PCT/US2013/051011, International Search Report mailed Oct. 29, 2013", 4 pgs.

(Continued)

*Primary Examiner* — Christopher A Flory
(74) *Attorney, Agent, or Firm* — Schwegman Lundberg & Woessner, P.A.

(57) ABSTRACT

An implantable medical device (IMD) may include multiple power supply circuits and an electrostimulation therapy output circuit configured to, in response to a control signal specifying an electrostimulation therapy, controllably connect any one or more of the first or second power supply circuits to any one or more of a first electrostimulation output node or a second electrostimulation output node to deliver an electrostimulation. In an embodiment, the IMD may include an electrostimulation therapy return circuit configured to establish a return path for the electrostimulation delivered via one or more of the first electrostimulation output node or the second electrostimulation output node.

20 Claims, 6 Drawing Sheets

(51) Int. Cl.
*A61N 1/05* (2006.01)
*A61N 1/378* (2006.01)

(56) References Cited

U.S. PATENT DOCUMENTS

| | | | |
|---|---|---|---|
| 5,456,709 A * | 10/1995 | Hamedi | 607/138 |
| 5,690,692 A * | 11/1997 | Fleming | 607/50 |
| 5,941,906 A | 8/1999 | Barreras, Sr. et al. | |
| 6,443,978 B1 * | 9/2002 | Zharov | 607/91 |
| 6,450,942 B1 * | 9/2002 | Lapanashvili et al. | 600/16 |
| 7,519,428 B1 * | 4/2009 | Palmer | 607/57 |
| 8,052,600 B2 * | 11/2011 | Beck et al. | 600/301 |
| 8,478,404 B2 | 7/2013 | Maile et al. | |
| 8,634,910 B2 * | 1/2014 | Stahmann | 607/5 |
| 8,649,862 B2 * | 2/2014 | Ludwig et al. | 607/7 |
| 8,712,520 B2 * | 4/2014 | Stahmann | 607/9 |
| 8,718,761 B2 * | 5/2014 | Stahmann | 607/9 |
| 8,718,764 B2 * | 5/2014 | Stahmann | 607/17 |
| 2003/0130699 A1 * | 7/2003 | Kelly et al. | 607/5 |
| 2005/0107841 A1 * | 5/2005 | Meadows | A61N 1/0553 607/43 |
| 2005/0245994 A1 * | 11/2005 | Varrichio | A61N 1/14 607/60 |
| 2006/0224187 A1 * | 10/2006 | Bradley et al. | 607/2 |
| 2006/0224222 A1 * | 10/2006 | Bradley et al. | 607/116 |
| 2007/0276450 A1 * | 11/2007 | Meadows | A61N 1/0553 607/46 |
| 2007/0293914 A1 * | 12/2007 | Woods | A61N 1/36071 607/60 |
| 2008/0051767 A1 * | 2/2008 | Rossing et al. | 604/891.1 |
| 2008/0125833 A1 * | 5/2008 | Bradley et al. | 607/60 |
| 2008/0147135 A1 * | 6/2008 | Hareland | 607/7 |
| 2009/0062883 A1 * | 3/2009 | Meadows | A61N 1/0553 607/46 |
| 2009/0204170 A1 * | 8/2009 | Hastings et al. | 607/33 |
| 2010/0069977 A1 * | 3/2010 | Stahmann | 607/4 |
| 2010/0069980 A1 * | 3/2010 | Stahmann | 607/5 |
| 2010/0069984 A1 * | 3/2010 | Stahmann | 607/9 |
| 2010/0069985 A1 * | 3/2010 | Stahmann | 607/9 |
| 2010/0217259 A1 * | 8/2010 | Strauss | A61B 18/1233 606/38 |
| 2010/0256712 A1 * | 10/2010 | Varrichio | H02M 3/07 607/72 |
| 2010/0305631 A1 * | 12/2010 | Bradley et al. | 607/2 |
| 2011/0160803 A1 * | 6/2011 | Stessman | A61N 1/37 607/62 |
| 2011/0276103 A1 * | 11/2011 | Maile et al. | 607/9 |
| 2012/0136411 A1 * | 5/2012 | Bradley et al. | 607/45 |
| 2012/0277822 A1 * | 11/2012 | Trier | A61N 1/36071 607/46 |
| 2012/0283795 A1 * | 11/2012 | Stancer | A61N 1/3688 607/11 |
| 2014/0107719 A1 * | 4/2014 | Bornzin | A61N 1/3962 607/9 |
| 2014/0296699 A1 * | 10/2014 | Stessman | A61N 1/37 600/411 |

OTHER PUBLICATIONS

"International Application Serial No. PCT/US2013/051011, Written Opinion mailed Oct. 29, 2013", 7 pgs.
"International Application Serial No. PCT/US2013/051011, International Preliminary Report on Patentability mailed Feb. 26, 2015", 9 pgs.

* cited by examiner

THERAPY DELIVERY ARCHITECTURE FOR IMPLANTABLE MEDICAL DEVICE

CLAIM OF PRIORITY

This application claims the benefit of priority under 35 U.S.C. §119(e) of Vijayagopal et al., U.S. Provisional Patent Application Ser. No. 61/683,806, titled "THERAPY DELIVERY ARCHITECTURE FOR IMPLANTABLE MEDICAL DEVICE," filed on Aug. 16, 2012, which is hereby incorporated by reference herein in its entirety.

BACKGROUND

Active implantable medical devices (IMDs) may be used to treat a variety of symptoms or diseases. For example, an IMD may be used to generate therapeutic electrostimulation for delivery to one or more tissue sites, such as including one or more cardiovascular or neural targets. Such electrostimulation therapy may include one or more of a cardiac pacing therapy, a cardioversion or defibrillation therapy, a neural stimulation therapy that may include an autonomic modulation therapy (AMT), or one or more other electrostimulation therapies.

In generally-available IMDs, electrostimulation may be generated using power supplies or other circuitry dedicated or hardwired for use with a particular electrode combination, therapy mode, or tissue site. Such therapy modes may correspond to using a power supply circuit configured only for operation in a controlled-current mode for neurostimulation or a power supply circuit configured only for operation in a controlled-voltage mode for cardiac pacing. If multiple tissue sites are to be stimulated, such power supply or other circuitry generally includes dedicated power supplies for each lead or electrode configuration corresponding to a respective site. Such generally-available IMDs may provide only limited options regarding available electrode combinations or therapy modes. For example, an IMD configured for current-mode stimulation is generally not reconfigurable to provide voltage-mode stimulation.

OVERVIEW

An IMD may generate an electrostimulation to be delivered to a desired tissue site. Delivery of the electrostimulation may be via electrodes that may be included as a portion of an implantable lead assembly. The lead assembly may be mechanically and electrically coupled to the IMD to interface with circuitry included in the IMD.

The present inventors have recognized among other things that a proliferation of lead or electrode configurations may complicate the accompanying circuit configuration included in the IMD. In order to support electrostimulation in a variety of electrode configurations or using a variety of therapy modes, the present inventors have provided an electrostimulation output circuit topology that may include a "crossbar" or matrix configuration. Such a matrix configuration may be used universally across multiple device families (e.g., for one or more of cardiac therapy or neural stimulation therapy devices). Such a matrix configuration may also preserve electrostimulation flexibility, without wasting integrated circuit area or sacrificing power efficiency, and without requiring costly modification of the power supply or output switching circuit configuration for each particular implantable device family.

In an embodiment, an IMD may include multiple power supply circuits, such as a first power supply circuit and a second power supply circuit. The IMD may include an electrostimulation therapy control circuit, such as may be coupled to an electrostimulation therapy output circuit. The electrostimulation therapy output circuit may be configured to, in response to a control signal specifying an electrostimulation therapy, controllably connect any one or more of the first or second power supply circuits to any one or more of a first electrostimulation output node or a second electrostimulation output node to deliver an electrostimulation.

In an embodiment, the IMD may include an electrostimulation therapy return circuit coupled to the electrostimulation therapy control circuit and configured to establish a return path for the electrostimulation delivered via one or more of the first electrostimulation output node or the second electrostimulation output node. The first and second electrostimulation output nodes may be configured for coupling to one or more implantable electrodes for delivery of the electrostimulation to a specified tissue site, such as cardiac tissue site or to provide electrostimulation to one or more other targets (e.g., a neural target or a baroreceptor).

In an embodiment, the power supply circuits may be configured to provide one or more of a specified (e.g., constant) current, voltage, or energy. For example, a power supply bus node may be routed to any specified combination of electrostimulation output nodes, and such a bus node may be supplied with any one or more of a controllable current, voltage, or total energy to be delivered.

In an illustrative embodiment, an IMD may include a plurality of "N" power supply circuits, "M" electrostimulation output nodes, and "O" therapy return paths. An electrostimulation output circuit may be configured to controllably electrically connect any one or more of the "N" power supply circuits to any one or more of the "M" electrostimulation output nodes. A therapy return path circuit may be configured to connect any one or more therapy return paths, "O," to any one or more of the electrostimulation output nodes "M." Such therapy return paths may include one or more coupling capacitors, such as to establish a specified (e.g., adjustable) capacitance or to provide a particular specified capacitor to be used in maintaining a charge-balanced condition during or after delivery of an electrostimulation. Such coupling capacitors may be located elsewhere in the electrostimulation circuitry.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
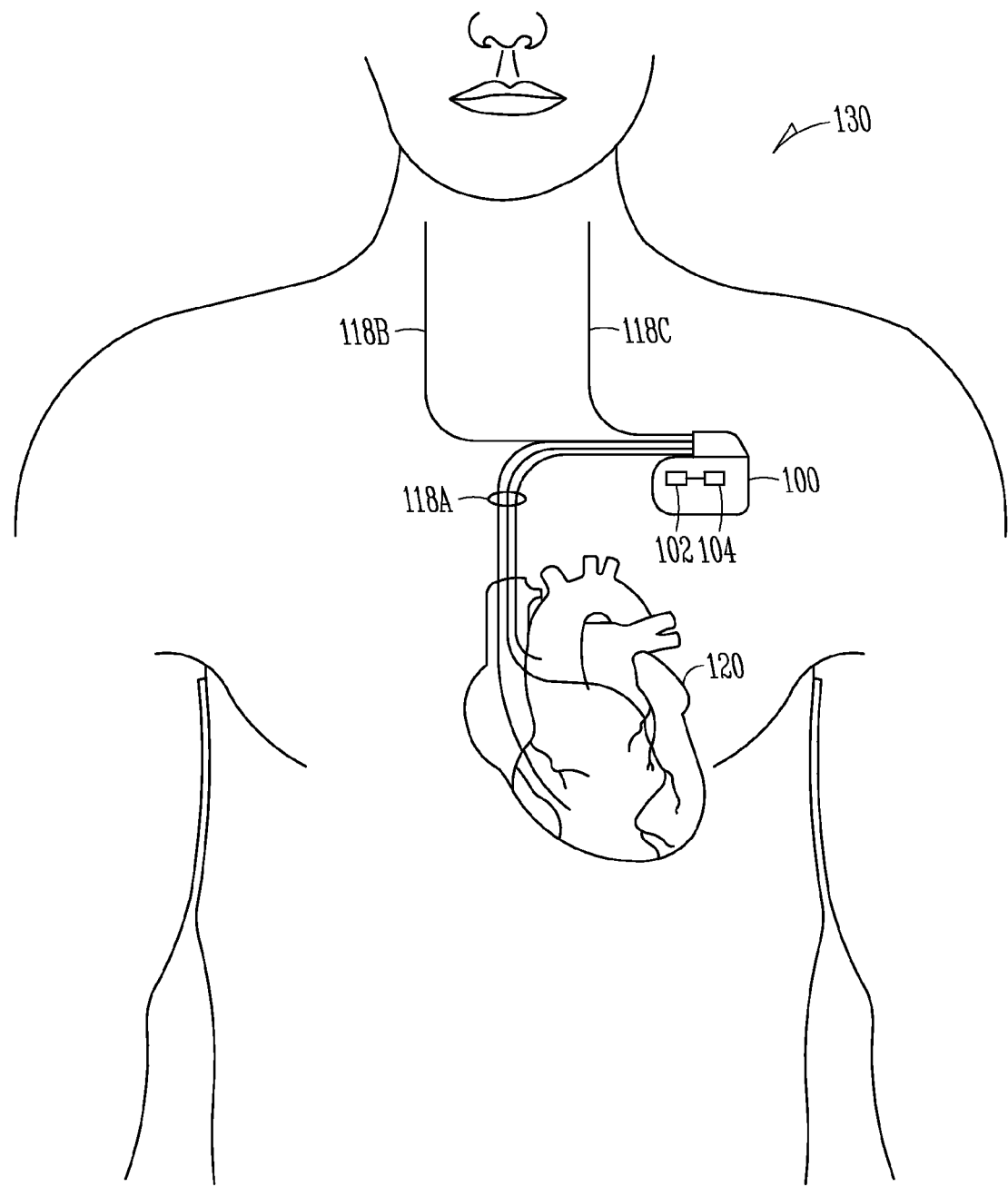
FIG. 1 illustrates generally an embodiment of a system including an active implantable medical device.

FIG. 1 illustrates generally an embodiment 130 that may include an active implantable medical device (IMD) 100. In the embodiment of FIG. 1, the IMD 100 may include various circuitry, such as a processor circuit 102, a memory circuit 104, or one or more other circuits such as shown in the embodiments of FIGS. 2 through 5. The IMD 100 may be located within a patient, such as subcutaneously or submuscularly. The IMD 100 may include one or more electrodes located on a housing of the IMD (e.g., a "CAN" electrode, or an "INDIFFERENT" electrode), or the IMD may be coupled to one or more implantable lead assemblies, such as one or more intravascularly-deliverable lead assemblies 118A. The one or more lead assemblies 118A may be configured to provide electrostimulation to one or more sites on, within, or near a heart 120. For example, such lead assemblies may include one or more electrodes located in the right-ventricular (RV) region, the right-atrial (RA) region, or the left-ventricular region (LV), such as accessed via one or more blood vessels. The IMD 100 may be coupled to one or more other lead assemblies, such one or more of a first or second non-cardiac-located lead assembly 118B or 118C, such as to provide electrostimulation of one or more neural or other targets. In an embodiment, electrostimulation generated by the IMD 100 may be coordinated with electrostimulation generated by one or more other implantable or external devices, or in response to information provided one or more other implantable or external devices (e.g., in response to sensed physiologic information such as a physiologic impedance, a patient's respiration, a patient's activity level, a patient's posture, or a sensed event indicative of intrinsic or evoked electrical activity such as cardiac or neural electrical activity).

The one or more of the lead assemblies 118A through 118C may include multiple electrodes coupled to corresponding conductors comprising such lead assemblies. Generally available electrostimulation devices may only offer a very limited number of possible electrode configurations for use in delivering an electrostimulation. For example, IMDs configured to provide one or more of bradycardia therapy or congestive heart failure (CHF) therapy, such as cardiac resynchronization therapy (CRT), may only offer electrode combinations such as a lead-tip-electrode-to-can (e.g., unipolar) configuration, or a lead-tip-to-lead-ring (bipolar) configuration.

In other embodiments, such as for CRT therapy, an LV lead may include multiple electrodes, and a generally-available IMD may offer only a very limited number of permutations of LV lead electrode configurations, including very few (if any) "tied" electrode or cross-chamber configurations. In contrast, the circuit configurations shown in the embodiments of FIGS. 2 through 5 illustrate generally a matrix-based or "crossbar" approach that may provide almost unlimited flexibility in selection of any electrode combination for use for electrostimulation. Such a matrix-based approach may also be used to provide simultaneous or at least partially contemporaneous electrostimulation at multiple sites either using independent electrostimulation power supply circuits or by electrically coupling multiple electrostimulation nodes together as a common cathode or a common anode (e.g., a "tied" electrode configuration).

Figure 2:
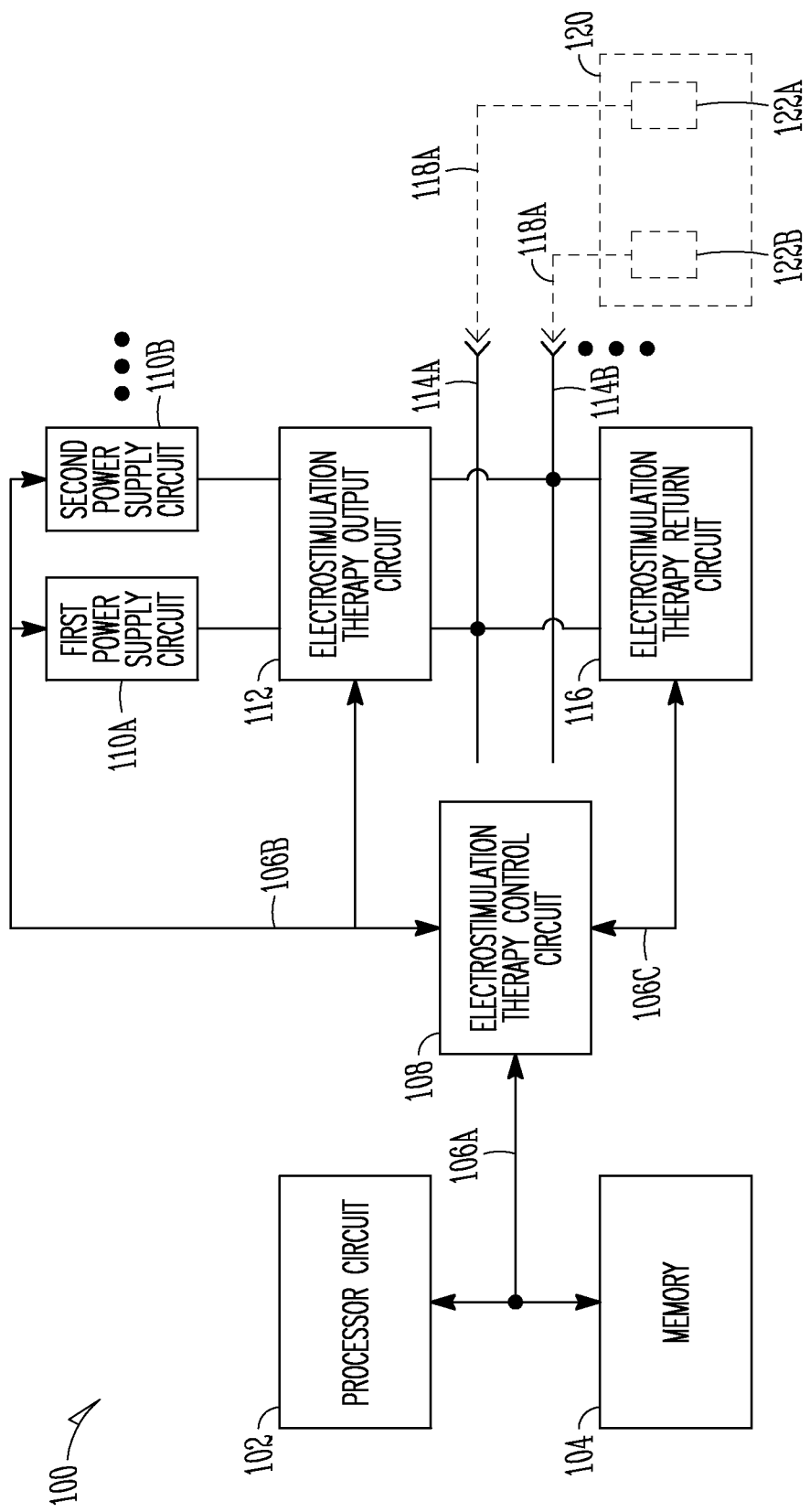
FIG. 2 illustrates generally an embodiment including at least a portion of an active implantable medical device.

FIG. 2 illustrates generally an embodiment that may include at least a portion of an active implantable medical device (IMD) 100. The IMD 100 may include a processor circuit 102, such as coupled via a first link 106A (e.g., a bus) to a memory circuit 104. The processor circuit may include or may be coupled to an electrostimulation therapy control circuit 108. The therapy control circuit 108 may be configured to provide an electrostimulation therapy control signal to one or more of a first power supply circuit 110A, a second power supply circuit 110B, or other power supply circuits, such as via a second link 106B. The therapy control circuit 108 may be configured to provide the electrostimulation therapy control signal to one or more of an electrostimulation therapy output circuit 112 such as via the second link 106B, or an electrostimulation therapy return circuit 116 such as via a third link 106C. The electrostimulation therapy output circuit 112 may be also coupled to one or more power supply circuits, such as the first or second power supply circuits 110A or 110B.

In response to the electrostimulation therapy control signal, one or more nodes in the electrostimulation therapy output circuit 112 may be coupled (e.g., controllably connected) to one or more of a first electrostimulation output node 114A or second electrostimulation output node 114B. Similarly, one or more nodes in the electrostimulation therapy return circuit 116 may be coupled (e.g., controllably connected) to one or more of the first or second electrostimulation output nodes 114A or 114B.

In an embodiment, a first implantable lead assembly 118A may be electrically coupled to the first electrostimulation output node 114A, such as to deliver an electrostimulation to a tissue site 120 using a first electrode 122A. A complete circuit may be formed, such as using a second electrode 122B coupled to a second implantable lead assembly 118B that may be coupled to a second electrostimulation output node 114B. In this manner, the complete circuit may comprise an electrostimulation path established through or applied across a tissue site, using one or more of the first or second power supply circuits 110A or 110B, the electrostimulation therapy output circuit 112, one or more of the first or second electrostimulation output nodes 114A or 114B, one or more of the first or second implantable lead assemblies 118A or 118B, one or more of the first or second electrodes 122A or 122B, the electrostimulation therapy return circuit 116, and a reference node (e.g., such as may be denoted "CAN," "GROUND," or "REF").

The first or second power supply circuits 110A or 110B may provide one or more of a specified (e.g., constant) voltage, a specified (e.g., constant) current, or a specified total energy. For example, the first or second power supply circuits may include a switched-capacitor configuration, a switched-inductor configuration, a controlled-current configuration, or one or more other topologies, such as including a specified output polarity. Accordingly, the terms "electrostimulation therapy output circuit" and "electrostimulation therapy return circuit" need not restrict current flow to a particular direction. Using such power supply circuits 110A or 110B, an electrostimulation may be generated having a specified constant current or voltage amplitude, or having a specified peak amplitude or corresponding specified "droop," along with a specified polarity. In this manner, any one or more of the first electrostimulation output node 114A or the second electrostimulation output node 114B may be assigned as an anode or cathode.

The first, second, or third links 106A through 106C may include respective or combined conductive couplings configured to carry control information, or one or more of the first, second, or third links 106A through 106C may include a digital communication bus. In an embodiment, the electrostimulation therapy control circuit may access the memory circuit 104 using Direct Memory Access (DMA) or otherwise without requiring the intervention of the processor circuit 102, such as to retrieve a table or matrix of power supply circuit 110A or 110B, electrostimulation therapy output circuit 112, or electrostimulation therapy return circuit 116 configurations, such as for use in delivering a programmed sequence electrostimulation pulses.

One or more of the processor circuit 102, the memory circuit 104, the electrostimulation therapy control circuit 108, the first or second power supply circuits 110A or 110B, the electrostimulation therapy output circuit 112, or the electrostimulation therapy return circuit 116 may be co-integrated or otherwise located within a commonly-shared integrated circuit, or within a commonly-shared integrated circuit package, such as within a biocompatible hermetically-sealed housing of the IMD 100.

Figure 3:
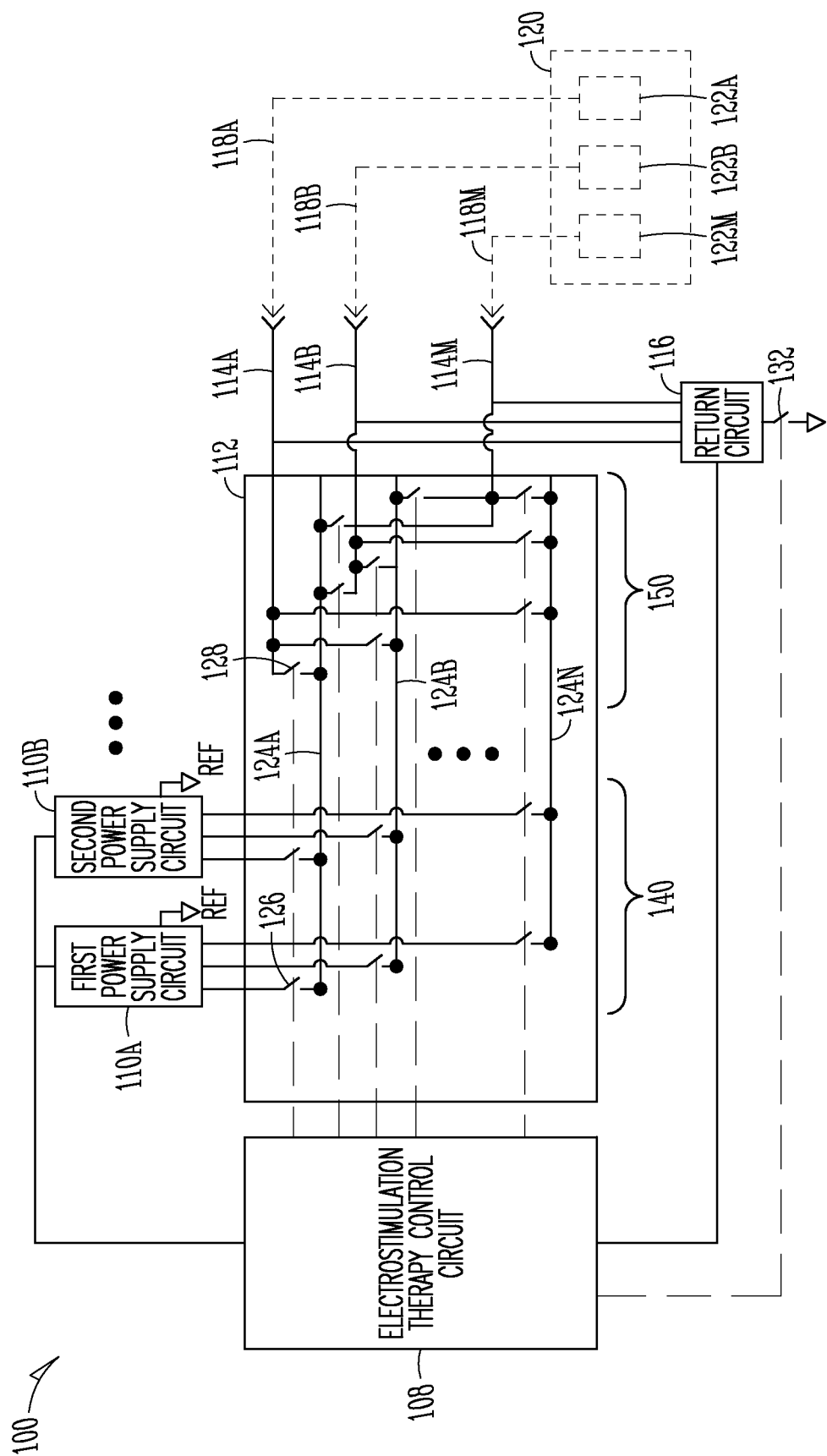
FIG. 3 illustrates generally an embodiment that including at least a portion of an active implantable medical device.

FIG. 3 illustrates generally an embodiment that may include at least a portion of an active implantable medical device (IMD) 100. The IMD 100 may include a plurality of power supply circuits, such as a first power supply circuit 110A or a second power supply circuit 110B. As in the embodiment of FIG. 2, the first or second power supply circuits 110A or 110B may be controllably connected to a reference node, REF. An electrostimulation therapy output circuit 116 may include an array of power supply selection switches 140 (e.g., one or more solid state or mechanical switches). For example, a power supply selection switch 126 may be used to couple the first power supply circuit 126 to a first power supply bus 124A. The power supply selection switches 140 may be configured to allow any one or more of the plurality of power supplies to be controllably connected to any one or more of the first power supply bus 124A, a second power supply bus 124B, or an "Nth" power supply bus 124N, such as in response to a control signal provided by an electrostimulation therapy control circuit 108.

The electrostimulation therapy output circuit 112 may include an array of therapy delivery switches 150, such as including a first therapy delivery switch 128. For example, the array therapy delivery switches 150 may be configured to controllably connect any one or more of the power supply busses 124A, 124B, through 124N, to any one or more of a plurality of electrostimulation output nodes, such as a first electrostimulation output node 114A, a second electrostimulation output node 114B, or an "Mth" electrostimulation output node 114M, such as in response to a control signal provided by the electrostimulation therapy control circuit 108.

A therapy return circuit 116 may provide a return path from any one or more of the electrostimulation output nodes 114A through 114M, such as to provide a complete circuit back to one or more of the power supplies 124A or 124B. One or more return switches, such as a return switch 132, can be used to controllably connect such as via a reference node, REF. In this manner, any one or more of the electrostimulation output nodes 114A through 114M may be assigned as a cathode or an anode.

Figure 4:
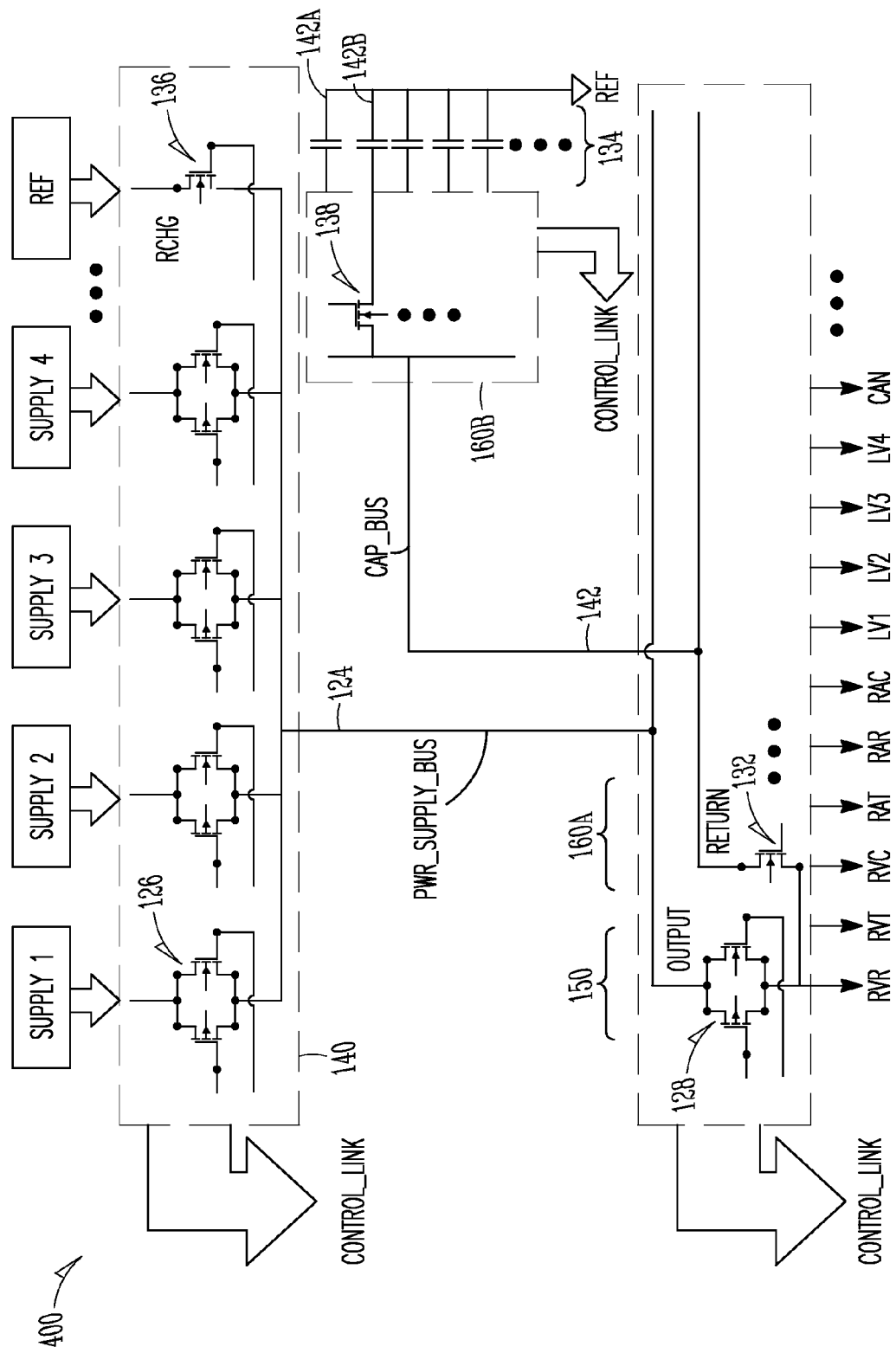
FIG. 4 illustrates generally an embodiment including at least a portion of an electrostimulation circuit, such as may be included in an active implantable medical device.
Figure 5:
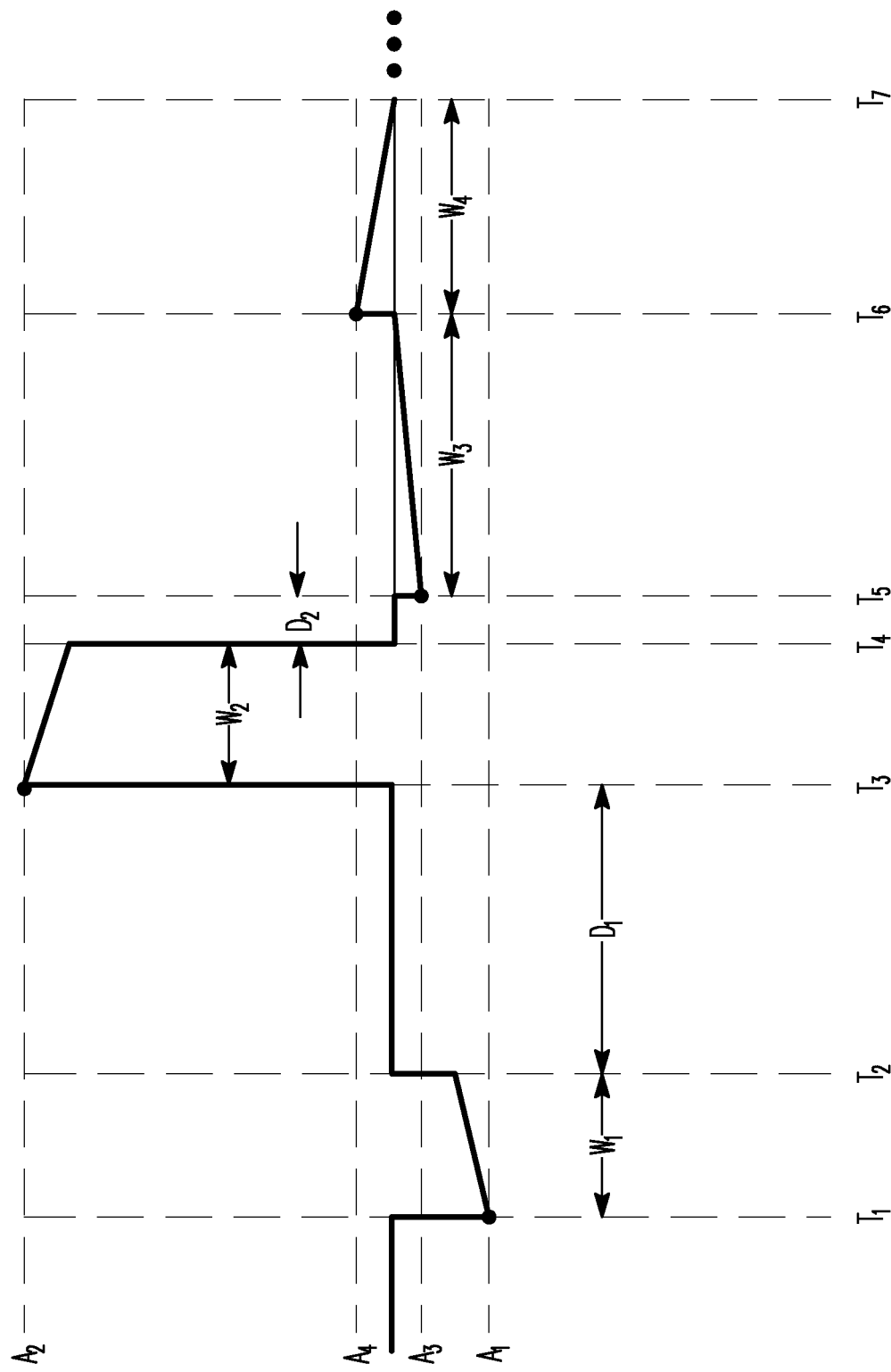
FIG. 5 illustrates generally an embodiment of an electrostimulation waveform, such as may be generated using circuitry shown in the examples of one or more of FIG. 1 through FIG. 4.

As shown in the embodiment of FIG. 4, one or more capacitors may be included, such as in series with an electrostimulation therapy delivery pathway or "vector." Such a series (e.g., alternating-current (AC) "coupling") capacitor may be included as a portion of one or more of the return circuit 116, one or more power supply circuits, along one or more power supply busses (e.g., the first power supply bus 124) or elsewhere. As shown in the embodiments of FIGS. 4 and 5, a charge-balanced or neutral condition may be maintained for a particular stimulus pathway or vector such as using a specified capacitor configuration for both delivery of an electrostimulation through the series capacitor, and for providing a "recharge" duration where such a capacitor may be connected across the previously-used specified therapy delivery electrodes to neutralize any residual polarization at the tissue site due to prior stimulation. Such a recharge may be initiated by a switch, such as a return switch 132, coupled to a reference node, REF.

FIG. 4 illustrates generally an embodiment that may include at least a portion of an electrostimulation circuit 400, such as may be included in an active implantable medical device (IMD). Similar to the embodiments discussed above in relation to FIGS. 2 and 3, the electrostimulation circuit 400 may include an array of two or more power supply circuits, such as four power supply circuits denoted SUPPLY 1 through SUPPLY 4. Such power supply circuits may be controllably connected to any one or more power supply busses, such as a first power supply bus 124, denoted PWR_SUPPLY_BUS. Such controllable coupling can be in response to a control signal provided by a link or bus, such as denoted CONTROL_LINK. Such a control signal can be used to control a state of one or more switches included in a power supply switch array 140, such as a first power supply switch 126 (e.g., a transmission gate structure including respective field-effect transistors).

A return path can be established such as a using a return switch array 160A included as a portion of a return circuit. The array 160A of such return switches can be used to connect any one or more electrostimulation output nodes to one or more capacitor busses, such as a capacitor bus 142, denoted CAP_BUS, using a first return switch 132. Such electrostimulation output nodes can include one or more terminals to be connected to one or more corresponding tissue-located electrodes, such as Right-Ventricular-Ring (RVR) electrode, a Right-Ventricular-Tip (RVT) electrode, a Right-Ventricular-Coil (RVC) electrode, a Right-Atrial-Tip (RAT) electrode, a Right-Atrial-Ring (RAR) electrode, a Right-Atrial-Coil (RAC) electrode, Left-Ventricular First through Fourth electrodes (LV1 through LV4), a CAN electrode, or one or more other electrodes. By way of example, other electrodes may include neural stimulation electrodes. Examples of neural stimulation electrodes include, but are not limited to, nerve cuffs such as a cervical vagus nerve cuff, intravascularly-fed nerve electrodes for transvascular stimulation of nerve targets, or electrodes configured to be attached in or proximate to neural targets. By way of example and not limitation, neural targets may include baroreceptor or chemoreceptor regions, nerve trunks such as the vagus nerve, glossopharyngeal nerve, carotid sinus nerve, hypoglossal nerve, renal nerve, etc., cardiac fat pads, or spinal nerves or nerve roots.

An array of capacitors 134, such as including a first capacitor 142A or a second capacitor 142B, can be controllably connected to any one or more capacitor busses, such as the capacitor bus 142, using a capacitor switch array 160B, including one or more transistor switches such as a first capacitor switch 138. For example, the switch array 160B can include a matrix of switches so that any one or more capacitors included in the capacitor array 134 can be controllably coupled between any one or more capacitor busses and a reference node, REF. In this manner, the capacitor array can provide a coupling capacitor arrangements that can be uniquely associated with particular output node configurations, such as including a specified capacitance value determined at least in part by specifying which capacitors in the array to combine in parallel for a given electrostimulation pathway or vector.

If a particular charge is established on a respective coupling capacitor (e.g., the first capacitor 142A) for a particular electrode configuration, the switch array 160B can be used to establish a recharge pathway including the same respective capacitor (or capacitors) to provide charge balance after electrostimulation, such as to suppress an unwanted afterpotential or polarization artifact for that particular electrode configuration.

As discussed in the embodiment of FIG. 4, after delivery of an electrostimulation, a tissue site can present such an afterpotential or polarization artifact, due to charge accumulation at an electrode-tissue interface. Such effects can adversely increase an electrostimulation capture threshold or can be erroneously detected as an intrinsic event such as a cardiac contraction when no such contraction has occurred. Over an extended period, such an afterpotential can accelerate corrosion or degradation of an electrode such as due to electrochemical or bio-affected corrosion effects. To suppress or eliminate such afterpotential or polarization, a recharge switch 136 can be used, such as to couple a respective power supply bus 124 to a reference node (e.g., REF), instead of the one or more power supply circuits after delivery of an electrostimulation but otherwise using the same electrostimulation output switch 128 and capacitor switch 160B configuration (e.g., the power supply switch 126 can be opened, but other switching can remain unchanged).

Such a "passive" recharge may use the selected coupling capacitors to passively bleed the excess charge from the electrode-tissue interface via the selected output nodes. In an illustrative example, an electrostimulation can be delivered between an RVT output node (e.g., such as assigned as a cathode) and an RVR output node (e.g., such as assigned as an anode), using a first power supply. Then, after delivery of the electrostimulation, the coupling capacitor configuration that was used during delivery of the electrostimulation can be re-established between the RVT and RVR output nodes to allow any accumulated charge to flow back into the coupling capacitor. Alternatively, an "active" recharge can be used, such as by generating and applying an electrostimulation having an opposite polarity and correspondingly opposite charge to neutralize such a polarization artifact, such as either using a first power supply circuit in a reversed polarity configuration, or using a second power supply circuit. The amplitude of such an "active" recharge need not be the same as the amplitude used during an initial electrostimulation. A duration of the "active" recharge can be correspondingly adjusted to provide a net neutral charge after a combination of an electrostimulation delivery and a corresponding "active" recharge event.

The embodiment of FIG. 4 shows the switch array 160B and capacitor array 134 arranged on a return side of the electrostimulation circuit 400, but the capacitor array 134 or switch array 160B need not be located in this portion of the electrostimulation circuit. For example, the capacitor array 134 and switch array 160B may be located in series with the one or more power supply busses (e.g., to allow selection of a specified capacitor included in the capacitor array 134, to be controllably placed in series between the first power supply switch 126 and the electrostimulation output switch 128), or elsewhere. Other passive or active components can be included in the electrostimulation circuit, such as one or more transient voltage suppressors, resistors, or capacitors (e.g., to provide circuit protection or to establish one or more desired high low-pass or high-pass filter configurations).

To complete the electrostimulation pathway, an array of therapy delivery switches 150 can include one or more electrostimulation output switches, such as a first electrostimulation output switch 128 (e.g., a transmission gate structure). One or more of the first power supply switch 126 or the first electrostimulation output switch 128 can be used to initiate or terminate generation of an electrostimulation (e.g., the last switch to complete the electrostimulation pathway may be used to toggle delivery or suppression of the electrostimulation by completing or opening the electrostimulation circuit). The switch used for initiating or terminating electrostimulation can be specified to provide desired on or off characteristics (e.g., a low resistance when conducting, a specified turn-on or turn-off time, or a specified reverse breakdown or holdback voltage).

In the embodiments discussed above and below, a single electrostimulation output node may be configured as an anode or cathode, however other configurations are possible, such as including multiple nodes electrically coupled to provide a common anode or common cathode (e.g., to establish a "tied" electrode configuration).

FIG. 5 illustrates generally an embodiment of an electrostimulation waveform 500, such as may be generated using circuitry shown in the embodiments of one or more of FIG. 1 through FIG. 4. The amplitudes of various portions of the waveforms shown in FIG. 5 may be specified current amplitudes, such as in relation to a specified neurostimulation waveform, or specified voltage amplitudes, such as in relation to a specified cardiac pacing or other electrostimulation waveform. The waveform 500 of FIG. 5 is intended to be illustrative, such as showing a multi-phasic waveform. Other waveforms may be generated according the embodiments discussed above and below, such as a monophasic pulse (e.g., single pulse), a bi-phasic pulse, a tri-phasic pulse, or one or more other types or sequences of pulses having a specified voltage or current amplitude or duration.

In FIG. 5, at a first time, T1, a first pulse amplitude, A1, can be established. Referring back to FIG. 4, such an amplitude can correspond to an output amplitude of a power supply circuit. Such an amplitude may be programmable or fixed, or established using one or more of a voltage or current divider or mirror circuit. After a specified duration, W1, the pulse can be truncated at a second time, T2. In FIG. 5, the pulse is shown as drooping back towards a reference amplitude, REF. However, in other examples, the pulse may be generated by a supply capable of maintaining a relatively constant output amplitude over the specified first pulse duration, W1. A specified first inter-phase duration, D1, may separate the first pulse from a second pulse. D1 may be programmable, though a minimum interval may be established such as by a switching latency or a reconfiguration latency of the electrostimulation output circuit.

At a third time, T3, after the specified first inter-phase duration, D1, a second pulse amplitude, A2, can be established. Such a second pulse can have a specified polarity, such as opposite the polarity of the first pulse (e.g., the "cathode" output node established during the first pulse can be assigned as the "anode" for the second pulse). The second pulse need not be the same "mode" as the first pulse. For example, the first pulse may be a voltage-mode pulse, and the second pulse can be a current-mode pulse having a specified peak current amplitude. After a specified second pulse duration, W2, the second pulse can be terminated at T4.

At T5, such as after a second inter-phase duration, D2, a third pulse amplitude, A3, can be established. The third pulse may be generated with a third power supply, or may be established using a "recharge" configuration as discussed in the embodiments above. For example, at T6, such as after a specified third pulse duration, W3, a fourth pulse can be immediately initiated, such as including a fourth pulse amplitude, A4. Depending on the switch configuration of the electrostimulation circuit, some combinations of switch states may provide little or no latency, such as if two successive "recharge" pulses are initiated. At T7, the fourth pulse can be terminated. In this manner, a variety of different waveform morphologies can be established.

The waveform 500 of FIG. 5 may be established according to a sequence of switch states that can be dynamically generated on-the-fly to provide a control signal for the electrostimulation circuit, such as using a microprocessor or application-specific integrated circuit (ASIC). In an embodiment, such a sequence of switch states can be stored in memory circuit, and such a sequence of "vectors" (e.g., a stimulation vector table) can be cycled through the electrostimulation circuit in sequence to provide a desired pattern or waveform. Such a sequence of control signals may be asynchronous or synchronous to an internal oscillator or clock circuit. In an example, such as during a fault condition, basic electrostimulation capability may be maintained such as by using control signals established independently of a microprocessor or a microprocessor clock circuit to provide a specified sequence of switch states according to such a vector table.

By way of example and not limitation, some embodiments may deliver an electrostimulation waveform to provide intermittent neural stimulation (INS) that alternates between intervals of stimulation being ON, when one stimulation pulse or a set of grouped stimulation pulses is delivered, and intervals of stimulation being OFF, when no stimulation pulses are delivered. The neural stimulation may use a controlled-current mode of electrostimulation. Thus, for example, some embodiments may deliver a plurality of monophasic or biphasic pulses within a neural stimulation burst. Pulses delivered within a neural stimulation burst may be delivered at a specified pulse frequency. Such pulses also have a specified amplitude. Both the pulse frequency and the pulse amplitude may be used to control the dose of the neural stimulation therapy. The duration of the stimulation ON interval may be referred to as a stimulation duration or a burst duration. The burst duration may also affect the dose of the neural stimulation therapy. The start of a stimulation ON interval may be referred to as a temporal reference point Neural Stimulation (NS) Event. A time interval between successive NS Events may be referred to as an INS Interval, which may also be referred to as a stimulation period or a burst period. The burst period or the number of neural stimulation events that occur over a time period may also affect the dose of the neural stimulation.

For an application of neural stimulation to be intermittent, the stimulation duration (e.g., ON interval) may generally be less than the stimulation period (e.g., INS Interval) when the neural stimulation is being applied. The duration of the OFF intervals of INS are generally determined by the durations of the ON interval and the INS Interval. The duration of the ON interval relative to the INS Interval (e.g., expressed as a ratio) is sometimes referred to as the duty cycle of the INS. A physician or clinician may control the adjustment of one or more neural stimulation parameters to control a stimulation intensity. For example, the dose of the neural stimulation may be titrated to provide a therapeutically or prophylactically effective dose of neural stimulation. The dose generally includes an amount or intensity of the neural stimulation at a given time frame, and also includes the number of times the neural stimulation is delivered over a period of time. The intensity of the neural stimulation may be adjusted by adjusting parameters such as amplitude, duty cycle, duration, and or frequency of the neural stimulation, or the number of neural stimulation events that occur over a period of time. Further, the polarity of the stimulation may be adjusted to accommodate different electrode configurations. For example, multipolar neural stimulation leads may be implanted.

The present subject matter may be used with different types of neural stimulation leads, and may be used to provide flexibility in determining whether a particular electrode will be used to deliver neural stimulation and whether the electrode will function as an anode or cathode. As an example, the neural stimulation electrodes may be configured into a tripolar electrode configuration to deliver unidirectional neural stimulation. As another example, by allowing one or more anode(s) and one or more cathode(s), the electric field used to stimulate a neural target may be tailored to provide effective stimulation of the neural target. The electric field may also be tailored to avoid undesired stimulation of other tissue (e.g., muscle or other nerves).

Figure 6:
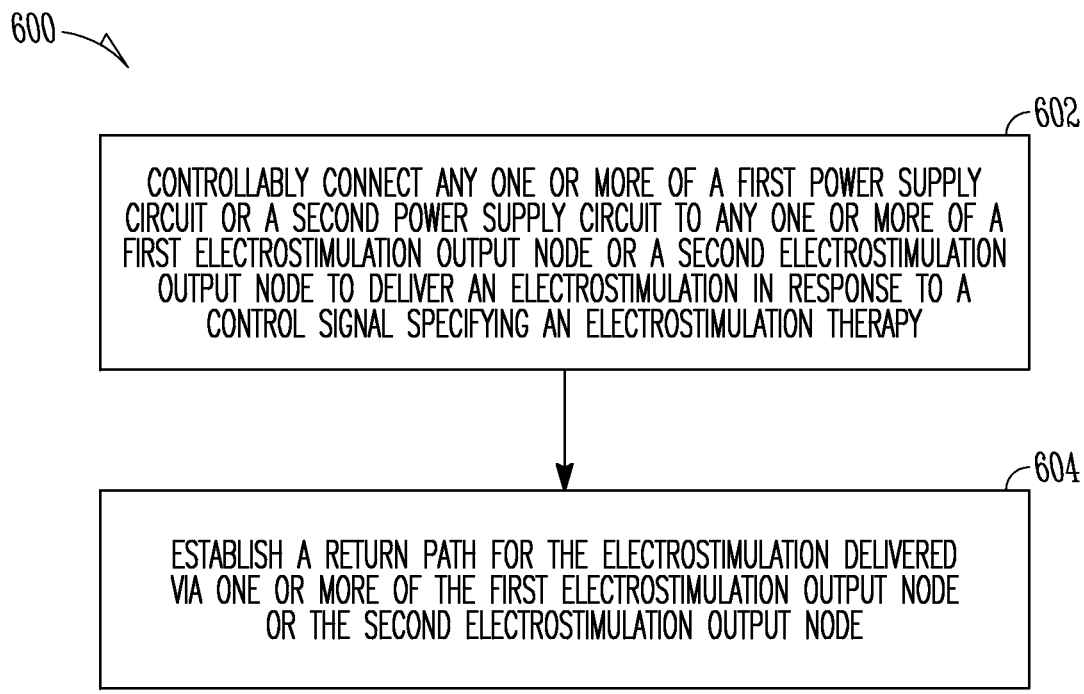
FIG. 6 illustrates generally an embodiment of a technique, such as a method, that may include controllably connecting a specified power supply to a specified output node.

FIG. 6 illustrates generally an embodiment of a technique, such as a method, that may include controllably connecting a specified power supply to a specified output node. At 602, a first power supply circuit or a second power supply circuit may be controllably connected to any one or more of a first electrostimulation output node or a second electrostimulation output node, such as in response to a control signal. Such a configuration can be used to deliver an electrostimulation to a specified tissue site using one or more electrodes that can be connected to respective electrostimulation output nodes.

At 604, a return path can be established for the electrostimulation delivered via one or more of the first electrostimulation output node or the second electrostimulation output node, such as in response to the control signal.

It is believed that the modular matrix-based output circuit configuration shown and discussed in the embodiments of FIGS. 1 through 6 can be used across multiple electrostimulation device families, such as providing maximum flexibility for supporting a variety of therapies. Such therapies may include using a quadripolar left-ventricular implantable lead configuration for a cardiac resynchronization therapy (CRT) device. Another therapy may include providing specified current-mode neurostimulation waveforms such as for one or more autonomic modulation therapies (AMT), or for other therapies such as pain management. An AMT therapy can be used to treat one or more of heart failure (HF), an over-active bladder (OAB), sleep apnea, or one or more other diseases or symptoms. Available electrostimulation output node configuration could be programmatically defined, such as via factory or field programming of a non-volatile memory to establish a preset family of available electrostimulation modes or output configurations.

Such presets may be established in part using information about a device model, or a therapy to be provided by the device (e.g., atrial-only, ventricular-only, dual-chamber, CRT, AMT). For experimental devices, access to a wider range of possible power supply circuit configuration or output node configurations may be "unlocked."

The embodiments discussed above refer to power supply circuits in plural, generically, but such "circuits" may include fewer actual regulated power supply circuits, such as configured to feed a voltage or current divider, or a current mirror structure. In this manner, one or more specified voltage or current sources can be established, supplied with energy by one or more shared power supply circuits. Such specified voltage or current sources can then be controllably switched to a selected power supply bus for generation of electrostimulation.

Modules and other circuitry shown and described herein may be implemented using software, hardware, firmware and/or combinations thereof. Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

The claimed invention is:

1. An implantable medical device, comprising:
a first power supply circuit;
a second power supply circuit;
an electrostimulation therapy control circuit, configured to provide a control signal specifying an electrostimulation therapy selected from a first electrostimulation therapy that uses the first power supply circuit and a second electrostimulation therapy that uses the second power supply circuit;
an electrostimulation therapy output circuit coupled to the electrostimulation therapy control circuit and the first and second power supply circuits, the electrostimulation therapy output circuit configured to respond the control signal by controllably connecting the first power supply circuit to one or more electrostimulation output nodes to deliver the first electrostimulation therapy or controllably connecting the second power supply circuit to one or more of the electrostimulation output nodes to deliver the second electrostimulation therapy; and
an electrostimulation therapy return circuit coupled to the electrostimulation therapy control circuit and configured to provide or maintain a charge-balance condition for the electrostimulation therapies, the electrostimulation therapy return circuit configured to respond to the control signal by establishing a first return path when the first electrostimulation therapy is selected and a second return path when the second electrostimulation therapy is selected, the first return path having a capacitance between at least one of the electrostimulation output nodes and a reference node to passively bleed charges to provide or maintain the charge-balanced condition during the first electrostimulation therapy, the second return path having a capacitance between at least one of the electrostimulation output nodes and the reference node to passively bleed charges to provide or maintain the charge-balanced condition during the second electrostimulation therapy;

wherein each of the electrostimulation output nodes is configured to couple to one or more implantable electrodes.

2. The implantable medical device of claim 1, wherein the electrostimulation therapy return circuit comprises an array of two or more capacitors and two or more switches each coupled to at least one of the two or more capacitors, and wherein the electrostimulation therapy return circuit is electrically coupled between a reference node and one or more of the electrostimulation output nodes via a capacitance established using one or more capacitors controllably selected from the array of two or more capacitors according to the selection of the first or second electrostimulation therapy.

3. The implantable medical device of claim 1, wherein the electrostimulation therapy includes a neural stimulation therapy, and the one or more electrostimulation output nodes are configured for coupling to the one or more implantable electrodes for delivery of the electrostimulation to a neural tissue site.

4. The implantable medical device of claim 1, wherein the electrostimulation therapy includes a cardiac pacing therapy, and the one or more electrostimulation output nodes are configured for coupling to the one or more implantable electrodes for delivery of the electrostimulation to a cardiac tissue site.

5. The implantable medical device of claim 1, wherein the first power supply circuit comprises a current-mode power supply circuit and wherein the second power supply circuit comprises a voltage-mode power supply circuit.

6. The implantable medical device of claim 1, comprising a plurality of power supply circuits and a plurality of electrostimulation output nodes; and
wherein, in response to the control signal, the electrostimulation therapy output circuit and the electrostimulation therapy return circuits are configured to generate first and second at least partially contemporaneous electrostimulation therapies, to deliver the first electrostimulation therapy to a first tissue site using a first combination of the plurality of electrostimulation output nodes controllably connected to a first power supply circuit included in the plurality of power supply circuits, and to deliver the second electrostimulation therapy to a second tissue site using a second combination of the plurality of electrostimulation output nodes controllably connected to a second power supply circuit included in the plurality of power supply circuits.

7. The implantable medical device of claim 6, wherein the electrostimulation therapy output circuit includes power supply selection switches and therapy delivery switches, the power supply selection switches each coupled to at least one of the plurality of power supply circuits, the therapy delivery switches each coupled to at least one of the plurality of electrostimulation output nodes; and
wherein the control signal specifying the electrostimulation therapy defines a state of the power supply switches and the therapy delivery switches.

8. The implantable medical device of claim 7, wherein one or more of the power supply selection switches or the therapy delivery switches includes a transmission gate structure, and wherein the therapy output circuit and the therapy return circuit comprise a commonly-shared integrated circuit assembly.

9. The implantable medical device of claim 1, wherein the control signal specifying an electrostimulation therapy defines one or more of an electrostimulation morphology, a specification of an electrostimulation output node configuration, a specification of a power supply circuit configuration, or a specification of a return path configuration.

10. The implantable medical device of claim 1, wherein the electrostimulation therapy control circuit is configured to control generation of an electrostimulation for delivery via a combination of electrostimulation output nodes, the electrostimulation comprising a first amplitude and a first polarity during a first duration using the first power supply circuit, and a second amplitude and a second polarity during a second duration using the second power supply circuit.

11. The implantable medical device of claim 10, wherein the electrostimulation comp rises a bi-phasic waveform.

12. The implantable medical device of claim 10, wherein the electrostimulation comprises a multi-phasic waveform including two or more phases each corresponding to electrostimulation generated by at least one of the power supply circuits.

13. The implantable medical device of claim 1, further comprising an implantable lead including an electrode; and
wherein at least one of the electrostimulation output nodes is electrically coupled to the electrode via the implantable lead.

14. An implantable medical device, comprising:
a plurality of power supply circuits;
a plurality of electrostimulation output nodes;
an electrostimulation therapy control circuit, configured to provide a control signal specifying an electrostimulation therapy;
an electrostimulation therapy output circuit coupled to the electrostimulation therapy control circuit and configured to respond to the control signal by controllably connecting one or more of the plurality of power supply circuits to any specified one or more of the plurality of electrostimulation output nodes to deliver an electrostimulation therapy;
an electrostimulation therapy return circuit coupled to the electrostimulation therapy control circuit and configured to provide or maintain a charge-balance condition for the electrostimulation therapies, the electrostimulation therapy return circuit configured to respond to the control signal by establishing a return path having a capacitance between at least one of the plurality of electrostimulation output nodes and a reference node to passively bleed charges to provide or maintain the charge-balanced condition during the electrostimulation therapy;
wherein each of the respective electrostimulation output nodes is configured to couple to respective implantable electrodes;
wherein, under the control of the therapy control circuit, the electrostimulation therapy output circuit and the electrostimulation therapy return circuits are configured to generate two or more at least partially contemporaneous electrostimulation therapies for respective delivery at two different specified tissue sites using any specified combination of the plurality of electrostimulation output nodes; and
wherein the specified electrostimulation therapy includes a specified neural stimulation therapy.

15. An implantable medical device comprising:
at least one processor; and
at least one memory circuit;
wherein the at least one memory circuit includes instructions that, when performed by the at least one processor, cause the implantable medical device to:
controllably connect a first power supply circuit to one or more electrostimulation output nodes to deliver a first electrostimulation therapy or controllably connect a second power supply circuit to one or more of the electrostimulation output nodes to deliver a second electrostimulation therapy in response to a control signal specifying an electrostimulation therapy and using an electrostimulation therapy output circuit coupled to an electrostimulation therapy control circuit and the first and second power supply circuits; and
provide or maintain a charge-balance condition for the electrostimulation therapies by establishing a first return path when the first electrostimulation therapy is selected and a second return path when the second electrostimulation therapy is selected, the first return path having a capacitance between at least one of the electrostimulation output nodes and a reference node to passively bleed charges to provide or maintain the charge-balanced condition during the first electrostimulation therapy using an electrostimulation therapy return circuit coupled to the electrostimulation therapy control circuit, the second return path having a capacitance between at least one of the electrostimulation output nodes and the reference node to passively bleed charges to provide or maintain the charge-balanced condition during the second electrostimulation therapy using the electrostimulation therapy return circuit coupled to the electrostimulation therapy control circuit;
wherein each of the electrostimulation output nodes is configured to couple to one or more implantable electrodes.

16. The implantable medical device of claim 15, wherein the instructions that cause the implantable medical device to establish the first or second return path include instructions to couple a reference node to one or more of the electrostimulation output nodes via a specified capacitance established using one or more capacitors included in an array of two or more capacitors.

17. The implantable medical device of claim 15, wherein the specified electrostimulation therapy includes a neural stimulation therapy or a cardiac pacing therapy.

18. The implantable medical device of claim 15, wherein the control signal specifying an electrostimulation therapy defines one or more of an electrostimulation morphology, a specification of an electrostimulation output node configuration, a specification of a power supply circuit configuration, or a specification of a return path configuration.

19. The implantable medical device of claim 15, wherein the first power supply circuit comprises a current-mode power supply circuit and wherein the second power supply circuit comp rises a voltage-mode power supply circuit.

20. The implantable medical device of claim 15, wherein the memory circuit includes instructions that cause the implantable medical device to generate two or more at least partially contemporaneous electrostimulation therapies, each of the two or more electrostimulation therapies delivered at one of two different tissue sites using plurality of electrostimulation output nodes controllably connected to one of a plurality of power supply circuits.

* * * * *